United States Patent
Akiyama et al.

(10) Patent No.: US 10,517,519 B2
(45) Date of Patent: Dec. 31, 2019

(54) BLOOD SAMPLING DEVICE AND BLOOD BAG SYSTEM

(75) Inventors: Masahiro Akiyama, Kanagawa (JP); Aya Hayakawa, Kanagawa (JP)

(73) Assignee: Terumo Kabushiki Kaisha, Tokyo (JP)

( * ) Notice: Subject to any disclaimer, the term of this patent is extended or adjusted under 35 U.S.C. 154(b) by 147 days.

(21) Appl. No.: 14/423,845

(22) PCT Filed: Aug. 31, 2012

(86) PCT No.: PCT/JP2012/072161
§ 371 (c)(1),
(2), (4) Date: Feb. 25, 2015

(87) PCT Pub. No.: WO2014/033911
PCT Pub. Date: Mar. 6, 2014

(65) Prior Publication Data
US 2015/0216465 A1 Aug. 6, 2015

(51) Int. Cl.
*A61B 5/00* (2006.01)
*A61B 5/15* (2006.01)
(Continued)

(52) U.S. Cl.
CPC .. *A61B 5/150992* (2013.01); *A61B 5/150519* (2013.01); *A61B 5/150572* (2013.01);
(Continued)

(58) Field of Classification Search
CPC .... A61M 2037/003; A61M 2037/0061; A61M 37/0015; A61M 5/150343;
(Continued)

(56) References Cited

U.S. PATENT DOCUMENTS 4,444,203 A * 4/1984 Engelman ......... A61M 25/0693
600/576
4,449,539 A * 5/1984 Sarstedt ............... A61M 5/344
600/577

(Continued)

FOREIGN PATENT DOCUMENTS

JP 62-148646 A 7/1987
JP 8-275933 A 10/1996
(Continued)

OTHER PUBLICATIONS

Japanese and English Translation of International Search Report for Application Serial No. PCT/JP2012/072161 performed by the Japanese Patent Office, dated Oct. 30, 2012, pp. 1-4.

*Primary Examiner* — May A Abouelela
(74) *Attorney, Agent, or Firm* — Terumo BCT, Inc IP Law Dept.

(57) ABSTRACT

A blood sampling device (10) configuring a blood bag system (12) includes: a hollow needle (80) that can penetrate through a rubber plug (202) of a blood sampling tube (200) inserted into a blood sampling holder (78); a hub (76) that includes a needle supporting unit (90) for supporting a base end side of the hollow needle (80) and to which the blood sampling holder (78) is rotatably attached; a needle cover (82) made of rubber that is externally fitted to the needle supporting unit (90) while covering a tip side of the hollow needle (80); and a cap (84) arranged on the needle supporting unit (90) in such a manner that the cap (84) can come into contact with the needle cover (82) and is independent of the blood sampling holder (78).

5 Claims, 6 Drawing Sheets

(51) Int. Cl.
*A61M 1/02* (2006.01)
*G01N 1/10* (2006.01)
*A61B 5/153* (2006.01)
*A61B 5/154* (2006.01)
*A61J 1/12* (2006.01)

(52) U.S. Cl.
CPC .. *A61B 5/150625* (2013.01); *A61B 5/150732* (2013.01); *A61M 1/0218* (2014.02); *G01N 1/10* (2013.01); *A61B 5/153* (2013.01); *A61B 5/15003* (2013.01); *A61B 5/154* (2013.01); *A61B 5/150351* (2013.01); *A61B 5/150366* (2013.01); *A61B 5/150389* (2013.01); *A61J 1/12* (2013.01); *A61M 1/0236* (2014.02); *G01N 2001/1031* (2013.01)

(58) Field of Classification Search
CPC ...... A61M 5/150389; A61M 5/150473; A61M 5/150534; A61M 5/150732; A61M 5/15074; A61M 5/155
USPC ......... 600/573, 576, 583, 577, 579; 604/110
See application file for complete search history.

(56) References Cited

U.S. PATENT DOCUMENTS

| | | | | |
|---|---|---|---|---|
| 4,782,841 A * | 11/1988 | Lopez | ................ | A61M 5/3243 600/577 |
| 4,819,659 A * | 4/1989 | Sitar | ................ | A61M 5/3243 600/577 |
| 4,850,374 A * | 7/1989 | Diaz-Ramos | ...... | A61B 5/15003 600/576 |
| 4,991,601 A * | 2/1991 | Kasai | ................ | A61B 5/15003 600/576 |
| 5,755,673 A * | 5/1998 | Kinsey | ................ | A61M 5/344 600/577 |
| 5,769,826 A * | 6/1998 | Johnson | ............ | A61M 5/3232 600/576 |
| 5,810,775 A * | 9/1998 | Shaw | ................ | A61B 5/15003 600/576 |
| 6,106,502 A * | 8/2000 | Richmond | ............... | A61J 1/10 604/246 |
| 6,146,337 A * | 11/2000 | Polidoro | ............ | A61M 5/3232 600/576 |
| 6,485,469 B1 * | 11/2002 | Stewart | ............ | A61M 5/3271 604/192 |
| 6,540,696 B1 * | 4/2003 | Dillon | ................ | A61B 5/15003 600/573 |
| 6,946,079 B1 * | 9/2005 | Holm | .................. | B01D 21/262 210/749 |
| 7,435,231 B2 * | 10/2008 | Mathias | ............. | A61M 1/0236 600/576 |
| 7,762,994 B2 * | 7/2010 | Klint | .................... | A61M 5/347 604/240 |
| 8,241,257 B2 * | 8/2012 | Wei | ..................... | A61M 5/2466 604/200 |
| 8,956,307 B2 * | 2/2015 | Morita | ................. | A61B 5/1438 600/573 |
| 2003/0208139 A1 * | 11/2003 | Crawford | .......... | A61B 5/15003 600/576 |
| 2004/0082899 A1 * | 4/2004 | Mathias | ............. | A61M 1/0236 604/6.16 |
| 2004/0147855 A1 | 7/2004 | Marsden | | |
| 2004/0199085 A1 * | 10/2004 | Young | ................ | A61B 5/15003 600/576 |
| 2005/0131315 A1 * | 6/2005 | Chu | ................ | A61B 5/150022 600/576 |
| 2005/0143712 A1 * | 6/2005 | Mathias | ............. | A61M 1/0209 604/409 |
| 2005/0165330 A1 * | 7/2005 | Orlu | ................. | A61B 5/15003 600/576 |
| 2005/0273019 A1 * | 12/2005 | Conway | ............ | A61B 5/15003 600/576 |
| 2005/0283093 A1 * | 12/2005 | Conway | ............ | A61B 5/15003 600/576 |
| 2005/0288607 A1 * | 12/2005 | Konrad | ............. | A61B 5/15003 600/576 |
| 2006/0015037 A1 * | 1/2006 | Konrad | ............. | A61B 5/15003 600/576 |
| 2006/0074349 A1 * | 4/2006 | Fan | ......................... | A61B 5/15 600/576 |
| 2006/0282060 A1 * | 12/2006 | Fujii | ................. | A61B 5/15003 604/403 |
| 2007/0129683 A1 * | 6/2007 | Brungardt | .............. | A61B 5/489 604/168.01 |
| 2008/0319346 A1 * | 12/2008 | Crawford | ............ | A61B 5/1422 600/577 |
| 2010/0241029 A1 * | 9/2010 | Mahurkar | .......... | A61B 5/15003 600/577 |
| 2012/0095368 A1 | 4/2012 | Morita et al. | | |
| 2013/0178760 A1 * | 7/2013 | Downie | ........... | A61B 5/150946 600/579 |

FOREIGN PATENT DOCUMENTS

| | | |
|---|---|---|
| JP | 2000-511635 A | 9/2000 |
| JP | 2012-016496 A | 1/2012 |
| WO | WO97/45714 A1 | 12/1997 |
| WO | WO2011001950 A1 | 1/2011 |

\* cited by examiner

FIG. 6

BLOOD SAMPLING DEVICE AND BLOOD BAG SYSTEM

TECHNICAL FIELD

The present invention relates to a blood sampling device equipped with a tubular blood sampling holder to which a blood sampling tube can be inserted, and a blood bag system.

BACKGROUND ART

In recent years, component transfusion of transfusing only the component necessary for a patient is being widely carried out. When carrying out such component transfusion, a blood bag system for dividing the blood (whole blood) sampled from a donor to a plurality of blood components, and accommodating and preserving the same is used.

In this type of blood bag system, a predetermined amount of blood (initial flow blood) that flows out immediately after inserting a blood sampling needle into the donor is accommodated in an initial flow blood bag, and the initial flow blood in the initial flow blood bag is transferred to a blood sampling holder with a blood sampling device to be used as a test blood for blood transfusion.

The blood sampling device includes, for example, a tubular blood sampling holder to which the blood sampling tube can be inserted, a hollow needle that can penetrate through a rubber plug (plug member) of the blood sampling tube, a hub that supports a base end side of the hollow needle and to which the blood sampling holder is attached, and a needle cover made of rubber that is externally fitted to the hub while covering the tip side of the hollow needle.

In this type of blood sampling device, when the blood sampling tube is inserted into the blood sampling holder, the needle cover is pushed and contracted in a longitudinal direction by the rubber plug of the blood sampling tube, and the hollow needle is exposed from the needle cover thus penetrating through the rubber plug. In this case, the needle cover is elastically deformed to an accordion form (waveform) so that a diameter becomes larger toward a radially outer side of the hollow needle, whereby the externally fitted portion of the needle cover with respect to the hub bulges and the fit-in force of the needle cover and the hub lowers.

The distal end portion of the needle cover may bite into the through-hole formed in the rubber plug, where if the blood sampling tube is pulled out from the hollow needle in such a state, the needle cover may be pulled by the rubber plug and fall out from the hub, and the initial flow blood may leak out from the blood sampling device as a result.

For the blood sampling device that solves such problem, the blood sampling device that prevents leakage of the initial flow blood (blood) from the blood sampling device by fixing a plate for preventing the accordion-like elastic deformation of the needle cover from reaching the externally fitted portion when the hollow needle is penetrated through the rubber plug of the blood sampling tube to the blood sampling holder (see e.g., JP 2012-16496 A) is known.

The blood sampling device in which a tubular body that surrounds the hub is arranged integrally with respect to the blood sampling holder, and the distal end portion of the tubular body is gradually diameter-reduced toward the needle tip side to be proximate to the externally fitted portion of the needle cover thus suppressing the needle cover from falling out from the hub is known (see e.g., U.S. Pat. No. 7,435,231).

SUMMARY OF INVENTION

Technical Problem

The blood sampling holder configuring the blood sampling device includes a tubular body to which the blood sampling tube can be inserted, and an open/close lid connected to the tubular body by way of a hinge. When using such blood sampling device, an operator preferably rotates the blood sampling holder with respect to the hub so that the open/close lid does not become an obstruction in the transferring task of the initial flow blood.

However, in the conventional technique described in JP 2012-16496A, the plate is fixed with respect to the blood sampling holder, so that when the blood sampling holder is rotated with respect to the hub, the plate is also rotated therewith. Thus, when the plate and the needle cover are brought into contact, the externally fitted portion of the needle cover may detach away from the hub thus lowering the fit-in force of the externally fitted portion and the hub, and the initial flow blood may leak out from the blood sampling device. This is the same for the conventional technique described in U.S. Pat. No. 7,435,231.

If the spacing of the needle cover and the plate is set wide to prevent such detaching away of the externally fitted portion, the accordion-like elastic deformation of the needle cover reaches the externally fitted portion and the needle cover may fall out from the hub.

In light of the foregoing, it is an object of the present invention to provide a blood sampling device that can prevent the externally fitted portion of the needle cover from detaching away from the hub when the blood sampling holder is rotated with respect to the hub and that can suppress the needle cover from falling out from the hub when drawing out the plug member of the blood sampling tube from the hollow needle, and a blood bag system.

Solution to Problem

[1] A blood sampling device according to the present invention includes a blood sampling holder to which a blood sampling tube is insertable; a hollow needle that penetrates through a plug member of the blood sampling tube; a hub that includes: a supporting unit for supporting a base end side of the hollow needle, and to which the blood sampling holder is rotatably attached; a needle cover made of rubber that is externally fitted to the supporting unit while covering a tip side of the hollow needle; and a fall-out preventing means arranged on the supporting unit independent from the blood sampling holder to prevent the needle cover from falling out from the supporting unit.

According to the blood sampling device of the present invention, the fall-out preventing means that prevents the needle cover from falling out from the supporting unit is arranged, so that even if the hollow needle is penetrated through the plug member of the blood sampling tube and the needle cover is elastically deformed to the accordion form, the needle cover can be suppressed from falling out from the supporting unit of the hub when pulling out the plug member from the hollow needle. Furthermore, since the fall-out preventing means is arranged on the supporting unit independent from the blood sampling holder, the fall-out preventing means does not rotate together with the blood sampling holder when rotating the blood sampling holder with respect to the hub. Thus, the needle cover can be prevented from detaching from the supporting unit when rotating the blood sampling holder with respect to the hub.

[2] In the blood sampling device described above, the fall-out preventing means may include a deformation regulating portion that is positioned on the tip side of the hollow needle than an externally fitted portion externally fitted to the supporting unit of the needle cover to make contact with or become proximate to the needle cover.

According to such configuration, the deformation regulating portion that makes contact with or becomes proximate to the needle cover is positioned on the tip side of the hollow needle than the supporting unit, so that the accordion-like elastic deformation of the needle cover can be suppressed from reaching the externally fitted portion. The externally fitted portion thus can be suppressed from bulging, and the fit-in force of the externally fitted portion and the supporting unit is held. The needle cover thus can be reliably suppressed from falling out from the supporting unit.

[3] In the blood sampling device described above, the deformation regulating portion may push the needle cover inward.

According to such configuration, the deformation regulating portion pushes the needle cover inward so that the frictional force of the needle cover and the supporting unit can be increased. The needle cover thus can be more reliably suppressed from falling out from the supporting unit.

[4] In the blood sampling device described above, the deformation regulating portion may be formed to an annular shape.

According to such configuration, the deformation regulating portion is formed to an annular shape, so that the accordion-like elastic deformation of the needle cover can be suitably suppressed from reaching the externally fitted portion, and the needle cover can be more reliably suppressed from falling out from the supporting unit.

[5] In the blood sampling device described above, the fall-out preventing means may include a surrounding portion that surrounds an externally fitted portion externally fitted to the supporting unit of the needle cover.

According to such configuration, the externally fitted portion of the needle cover is surrounded by the surrounding portion so that the externally fitted portion can be suitably suppressed from bulging. The fit-in force of the externally fitted portion and the needle cover thus can be reliably suppressed from lowering, whereby the needle cover is more unlikely to fall out from the supporting unit.

[6] In the blood sampling device described above, the fall-out preventing means may include a lock portion to be fitted to the supporting unit, a surrounding portion that extends from the lock portion toward a tip direction of the hollow needle and that surrounds the externally fitted portion, and the deformation regulating portion that is arranged extending from the surrounding portion and that has a reduced diameter than the surrounding portion.

According to such configuration, the lock portion is securely fixed with respect to the supporting unit, and the accordion-like elastic deformation is suitably suppressed from reaching the externally fitted portion by the diameter reduced deformation regulating portion, whereby the needle cover can be more effectively suppressed from falling out from the supporting unit.

[7] A blood bag system according to the present invention includes: an initial flow blood bag that accommodates an initial flow blood; a blood sampling device that transfers the initial flow blood in the initial flow blood bag to a blood sampling tube; a blood sampling bag that accommodates blood after the initial flow blood is removed; and a separation processing section that divides the blood accommodated in the blood sampling bag into a plurality of blood components, and that accommodates each component in a different bag; wherein the blood sampling device is the blood sampling device described above.

The blood bag system according to the present invention has effects similar to the blood sampling device described above.

DESCRIPTION OF EMBODIMENTS

The suitable embodiment for a blood sampling device and a blood bag system according to the present invention will be hereinafter described with reference to the accompanying drawings.

A blood bag system 12 is provided to centrifuge the blood containing a plurality of components into a plurality of components having different specific weights (e.g., three components of light specific weight component, middle specific weight component, and heavy specific weight component, or two components of light specific weight component and heavy specific weight component) and separately accommodate and preserve each component in a different bag.

The blood bag system 12 according to the present embodiment is configured to centrifuge the residual blood component, in which white blood cells and blood platelets are removed from the whole blood, into two components of plasma and concentrated red blood cell, and separately accommodate and preserve the plasma and the concentrated red blood cell in different bags.

Figure 1:
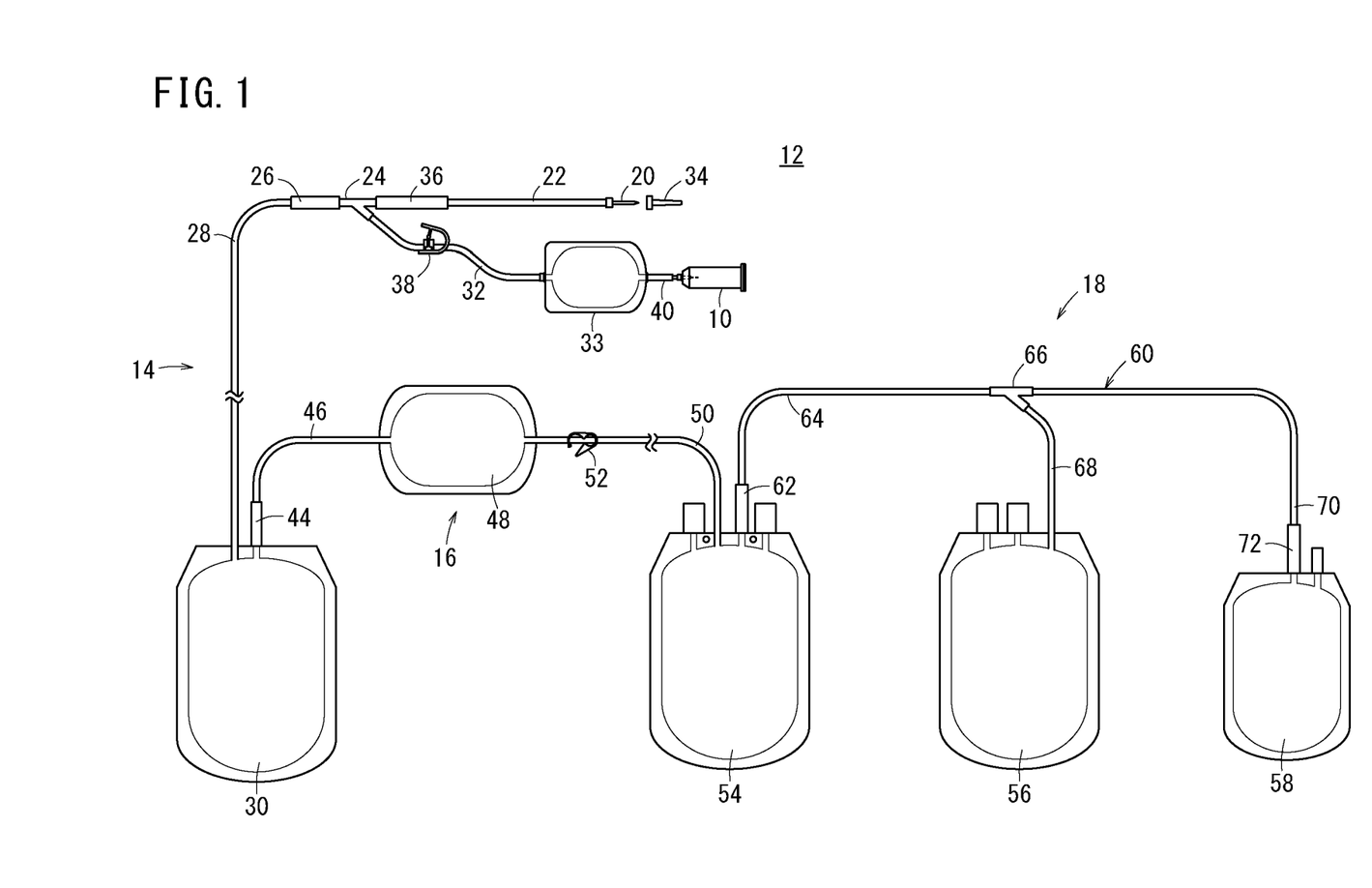
FIG. 1 is a plan view of a blood bag system according to one embodiment of the present invention.

As shown in FIG. 1, the blood bag system 12 includes a blood sampling section 14 for sampling blood (whole blood) from a donor, a pre-processing section 16 for removing a predetermined blood component from the whole blood, and a separation processing section 18 for centrifuging the residual blood component, in which a predetermined component is removed, to divide into plurality of blood components and accommodating (storing) each component in different bags.

The blood sampling section 14 includes a blood sampling needle 20, a first tube 22 having one end connected to the blood sampling needle 20, a Y-shaped branched connector 24 connected to the other end of the first tube 22, a second tube 28 connected to the branched connector 24 by way of a sealing member (breaking/communicating member) 26, a parent bag (blood sampling bag) 30 connected to the other end of the second tube 28, a branched tube 32 communicating to the first tube 22 by way of the branched connector 24, and an initial flow blood bag 33, connected to the other end of the branched tube 32, for accommodating (storing) a predetermined amount of blood (initial flow blood) that flows out immediately after inserting the blood sampling needle 20 into the donor.

A needle cap 34 is attached to the blood sampling needle 20 until before use, and a needle guard 36 is attached thereto after use. The needle guard 36 is arranged to be movable along the longitudinal direction on the first tube 22. The sealing member 26 is configured to close the flow path in the initial state, and open the flow path when a breaking operation is carried out.

A clamp 38 for closing and opening the flow path of the branched tube 32 is arranged at a middle portion of the branched tube 32. The clamp 38 is configured so as not to open after being closed once. A clamp similar to the clamp disclosed in JP 5-23792 A, for example, can be used for the clamp 38.

The initial flow blood bag 33 is configured to a bag shape by, for example, stacking a flexible sheet material made of soft resin such as polyvinyl chloride and polyolefin, and fusing (heat fusing, high frequency fusing) or adhering the seal portion at the peripheral edge. The parent bag 30 is similarly configured. A filter 48, a first child bag 54, a second child bag 56, and a medical solution bag 58, to be described later, are also similarly configured.

Figure 5:
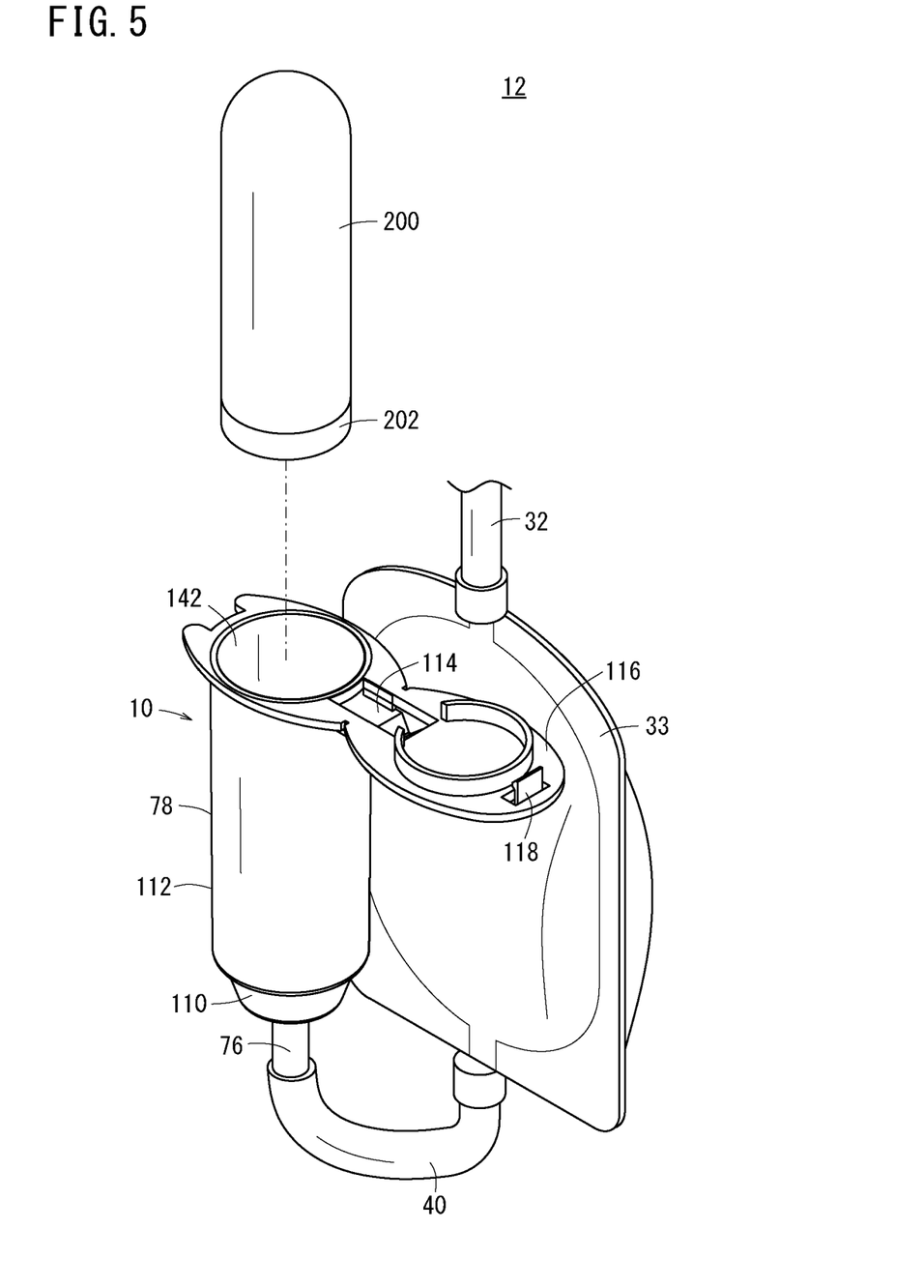
FIG. 5 is a perspective explanatory view showing a state in which a blood sampling tube is inserted into a blood sampling holder configuring the blood sampling device.

A blood sampling device 10 is connected to the initial flow blood bag 33 by way of an extraction tube 40, and a blood sampling tube 200 is attached to the blood sampling device 10 to transfer the initial flow blood in the initial flow blood bag 33 to the blood sampling tube 200 in a depressurized state (vacuum state) (see FIG. 5). The detailed description of the blood sampling device 10 will be described later.

The pre-processing section 16 includes an entrance side tube 46 connected to the parent bag 30 by way of a sealing member 44, the filter 48 for removing a predetermined cell (e.g., white blood cell and blood platelet) from the blood guided from the entrance side tube 46, and an exit side tube 50 for guiding the residual blood component, from which the predetermined cell is removed with the filter 48, to the separation processing section 18.

The sealing member 44 has the configuration and function similar to the sealing member 26. Sealing members 62, 72, to be described later, also have similar configuration and function. A clamp 52 for closing and opening the flow path of the exit side tube 50 is arranged at a middle portion of the exit side tube 50.

The separation processing section 18 includes the first child bag (first bag) 54 for accommodating (storing) the blood component guided from the exit side tube 50, the second child bag (second bag) 56 for accommodating and preserving the supernatant component obtained by centrifuging the blood component in the first child bag 54, the medical solution bag (third bag) 58 for accommodating a red blood cell preservative solution, and a transfer line 60 connected to the first child bag 54, the second child bag 56, and the medical solution bag 58.

The first child bag 54 serves as a bag for accommodating (storing) the residual blood component, in which the predetermined cell is removed with the filter 48, and also as a bag for preserving a sedimentation component (concentrated cell bloods) obtained by centrifuging the blood component.

The transfer line 60 includes a first tube 64 connected to the first child bag 54 by way of the breakable sealing member 62, a Y-shaped branched connector 66 connected to the other end of the first tube 64, a second tube 68 for connecting the branched connector 66 and the second child bag 56, and a third tube 70 for connecting the breakable sealing member 72 arranged in the medical solution bag 58 and the branched connector 66.

Figure 2:
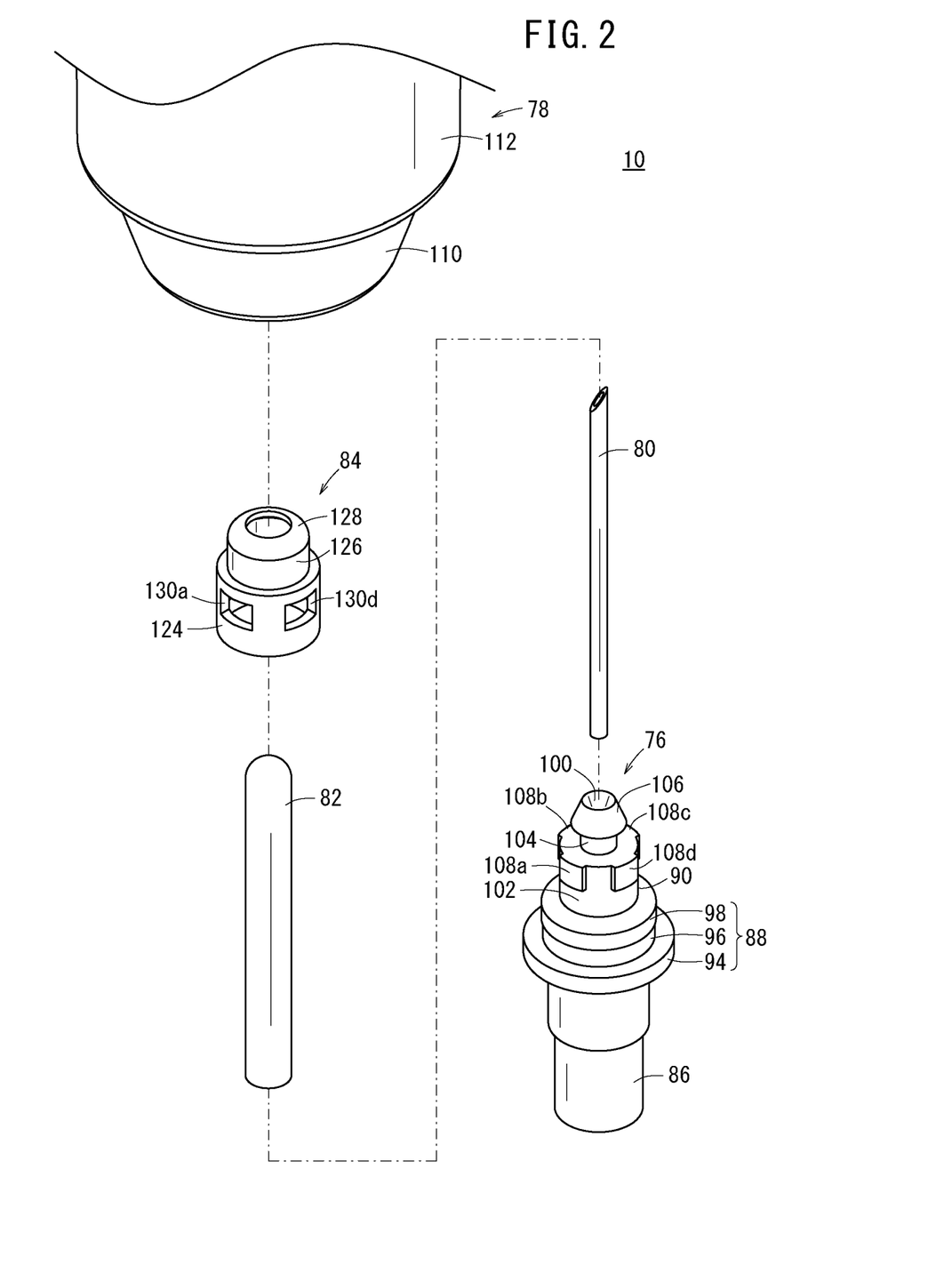
FIG. 2 is a partially omitted exploded perspective view of a blood sampling device according to one embodiment of the present invention.
Figure 3:
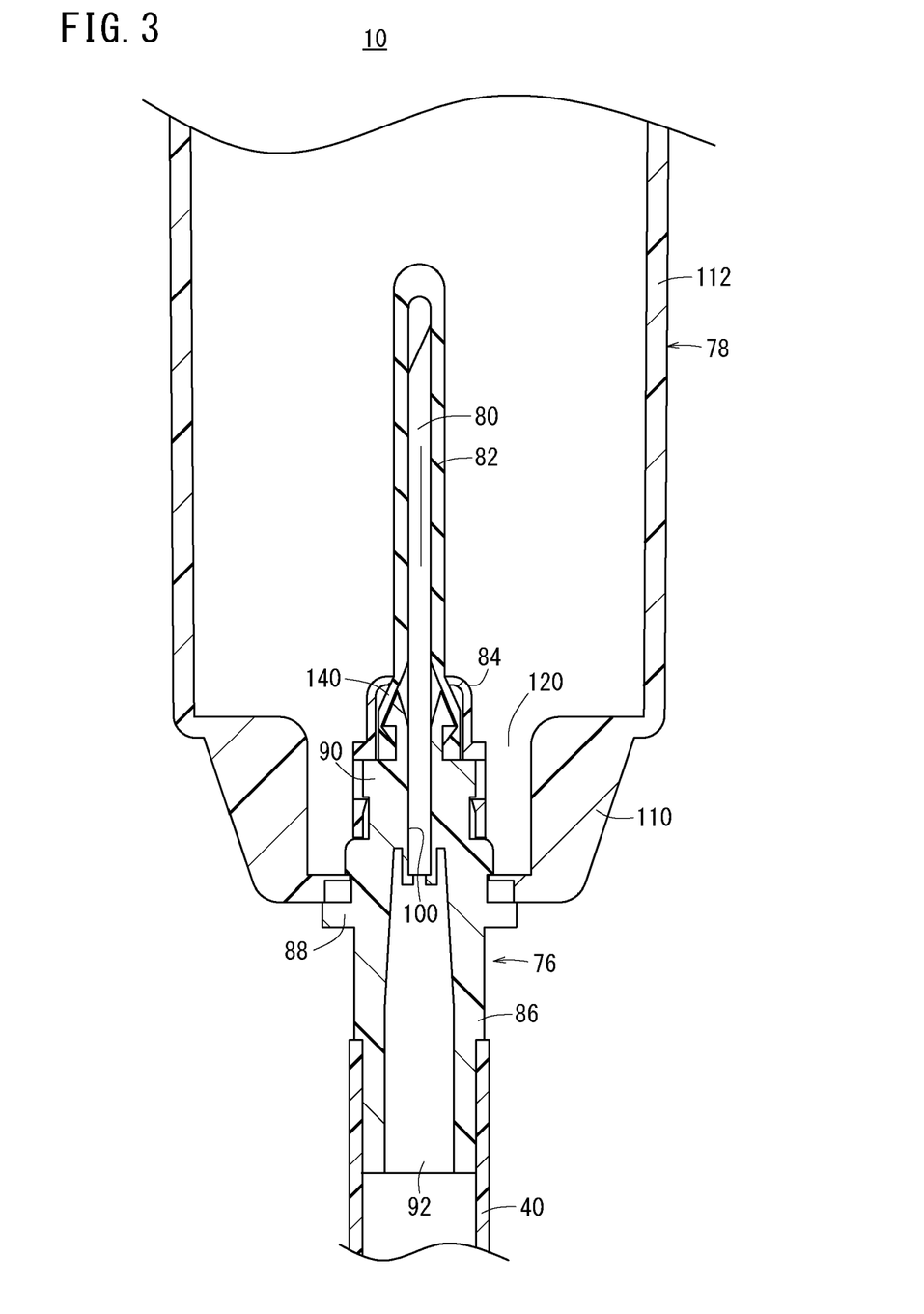
FIG. 3 is a partially omitted longitudinal cross-sectional view of the blood sampling device shown in FIG. 1.
Figure 4:
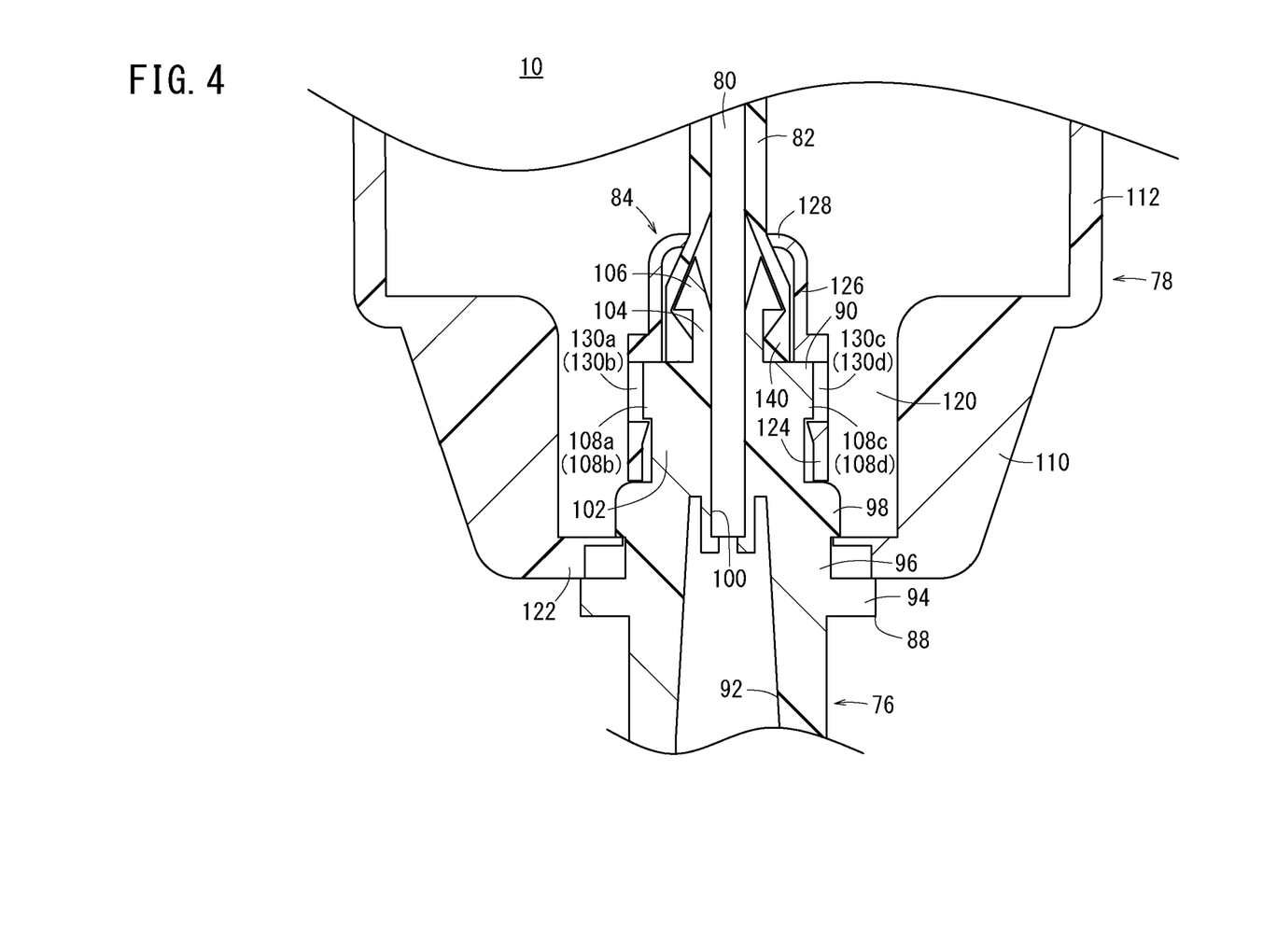
FIG. 4 is a partially enlarged cross-sectional view of FIG. 3.

The blood sampling device 10 according to the present embodiment will now be described. As shown in FIGS. 2 to 4, the blood sampling device 10 includes a hub 76, to which the extraction tube 40 connected to the initial flow blood bag 33 is connected, a blood sampling holder 78, attached to the hub 76 and to which the blood sampling tube 200 can be inserted, a hollow needle 80 that can penetrate through the rubber plug (plug member, see FIGS. 5 and 6) 202 of the blood sampling tube 200 while being arranged in the hub 76, a rubber needle cover 82 to be attached to the hub 76 while covering the tip side of the hollow needle 80, and a cap (fall-out preventing means) 84 for preventing the needle cover 82 from falling out from the hub 76.

In the following description, the tip side of the hollow needle 80 is referred to as "tip side" or the "tip direction", and the opposite side is referred to as "base end side" or "base end direction" with respect to the hub 76 and the configuring elements thereof.

The hub 76 is, for example, an integrated molded article made of resin, and the like, and is extended in one direction. The hub 76 includes a tube attaching unit 86 formed at the base end side, a holder attaching unit 88 arranged on the distal end side of the tube attaching unit 86, and a needle supporting unit 90 arranged on the distal end side of the holder attaching unit 88.

An initial flow blood passage 92 extending along the extending direction of the hub 76 is formed in the tube attaching unit 86 and the holder attaching unit 88. The holder attaching unit 88 is formed with a flange portion 94 arranged on the distal end side of the tube attaching unit 86, an intermediate portion 96 projected out toward the distal end side from the flange portion 94, and a plug portion 98 arranged on the distal end side of the intermediate portion 96. The plug portion 98 is formed to have a slightly larger diameter than the intermediate portion 96.

A needle insertion hole 100 extending in the longitudinal direction of the hub 76 and communicating to the initial flow blood passage 92 described above, is formed in the needle supporting unit 90. The needle supporting unit 90 includes a projection 102 projected out from a distal end face of the plug portion 98, a small diameter portion 104 projected out from the distal end face of the projection 102, and a large diameter portion 106 arranged on the distal end side of the small diameter portion 104.

A plurality of (four in the present embodiment) fit-in protrusions 108a to 108d that projects out radially outward is formed on the distal end side of the outer circumferential surface of the projection 102. The fit-in protrusions 108a to 108d are positioned at equal interval along the circumferential direction of the projection 102, where each fit-in protrusion 108a to 108d is formed to a rectangular shape in plan view.

The outer circumferential surface of the large diameter portion 106 is formed to a tapered shape in which the diameter gradually reduces toward the distal end side (tip side of the hollow needle 80). The inner circumferential surface configuring a part of the needle insertion hole 100 in the large diameter portion 106 is formed to a tapered shape in which the diameter gradually increases toward the distal end side. In the assembly step of the blood sampling device 10, the base end side of the hollow needle 80 can be inserted into the needle insertion hole 100 while being slidably moved on the inner circumferential surface of the large diameter portion 106 so that the insertion of the hollow needle 80 to the needle insertion hole 100 is facilitated.

The blood sampling holder 78 includes a base portion 110 attached to the holder attaching unit 88, a tubular body 112 having one end connected to the base portion 110, and an open/close lid 116 connected to the other end of the tubular body 112 by way of a hinge 114 (see FIG. 5). The open/close lid 116 includes a lock nail 118 that can be locked to the tubular body 112.

The base portion 110 is formed with an arrangement hole 120, to which the needle supporting unit 90 can be arranged, and an engagement portion 122 that is arranged between the flange portion 94 and the plug portion 98 configuring the hub 76, that projects out inward and that extends in the circumferential direction is formed on a wall surface configuring the arrangement hole 120. In other words, in the present embodiment, the engagement portion 122 is engaged so as to be sandwiched by the flange portion 94 and the plug portion 98, so that the blood sampling holder 78 is supported in a state rotatable about the axis line of the hub 76 with respect to the hub 76.

The hollow needle 80 can be made with an arbitrary material, and for example, can be made with various types of metal materials such as stainless steel, aluminum, aluminum alloy, titanium, titanium alloy, super elastic alloy such as Ni—Ti alloy, and the like, and various types of hard resin materials such as polyphenylene sulfide, and the like. The hollow needle 80 is supported by the needle supporting unit 90 configuring the hub 76 with the base end side inserted in the needle insertion hole 100.

The needle cover 82 can be made with various types of rubber materials such as, for example, natural rubber, isoprene rubber, butadiene rubber, styrene-butadiene rubber, nitrile rubber, chloroprene rubber, butyl rubber, acryl rubber, ethylene-propylene rubber, hydrin rubber, urethane rubber, silicon rubber, and fluorine contained rubber.

The needle cover 82 is extended along the hollow needle 80, and has the base end side externally fitted with respect to the small diameter portion 104 and the large diameter portion 106 configuring the hub 76. In other words, the needle cover 82 is held by the small diameter portion 104 and the large diameter portion 106 by the elastic force thereof. The inner surface of the needle cover 82 is brought into contact with the outer circumferential surface of the small diameter portion 104 and the tapered outer circumferential surface of the large diameter portion 106 in this state. The needle cover 82 covers the entire portion projecting out from the needle supporting unit 90 including the needle tip of the hollow needle 80.

The cap 84 is, for example, an integrated molded article made of resin, and the like, and includes a lock portion 124 to be attached to the needle supporting unit 90 configuring the hub 76, a surrounding portion 126 extending toward the distal end side from the lock portion 124, and a deformation regulating portion 128 arranged extending from the surrounding portion 126.

The lock portion 124 is configured to a tubular shape, and a plurality (same number as fit-in protrusions 108a to 108d described above, four in the present embodiment) fit-in holes 130a to 130d that passes through the inner/outer surface is formed on the circumferential wall. The fit-in holes 130a to 130d are positioned at equal interval along the circumferential direction of the lock portion 124, and each fit-in hole 130a to 130d corresponds to each fit-in protrusion 108a to 108d. As apparent from FIG. 4, the portion on the base end side of the wall portion configuring each fit-in hole 130a to 130d is projected out inward so that the thickness gradually becomes thicker toward the distal end side, where such projected portion makes contact with each fit-in protrusion 108a to 108d.

The surrounding portion 126 is formed to a tubular shape to surround a portion (externally fitted portion) 140 externally fitted to the small diameter portion 104 and the large diameter portion 106 of the needle cover 82. In the present embodiment, the surrounding portion 126 does not make contact with the externally fitted portion 140, but may make contact with the externally fitted portion 140.

The cap 84 can be easily attached with respect to the hub 76 if the surrounding portion 126 does not make contact with the externally fitted portion 140, but the externally fitted portion 140 can be reliably suppressed from elastically deforming so as to bulge radially outward if the surrounding portion 126 makes contact with the externally fitted portion 140.

The deformation regulating portion 128 is configured to an annular shape, and is positioned on the tip side of the hollow needle 80 than the large diameter portion 106 with the cap 84 fitted to the hub 76. The deformation regulating portion 128 pushes the needle cover 82 inward with the inner end. Thus, the inner surface of the needle cover 82 can be reliably brought into contact with respect to the tapered outer surface of the large diameter portion 106, and the frictional force of the needle cover 82 and the large diameter portion 106 can be increased.

The blood sampling device 10 configured as above is assembled in the following manner. In other words, the base end side of the hollow needle 80 is first inserted with respect to the needle insertion hole 100 of the hub 76. In this case, the base end side of the hollow needle 80 can be smoothly inserted into the needle insertion hole 100 since the inner surface of the large diameter portion 106 has a tapered shape in which the diameter is gradually increased toward the distal end side.

The needle cover 82 is then placed over the tip side of the hollow needle 80, and the small diameter portion 104 and the large diameter portion 106 are pushed into the inner hole while widening the base end side of the needle cover 82 radially outward. The needle cover 82 is thereby externally fitted with respect to the needle supporting unit 90.

The cap 84 is then passed through the needle cover 82 to attach the lock portion 124 to the needle supporting unit 90. Specifically, the cap 84 is pushed in with respect to the hub 76 so that each fit-in protrusion 108a to 108d of the needle supporting unit 90 fits into each fit-in hole 130a to 130d of the cap 84. The cap 84 is thereby fixed with respect to the hub 76.

The needle cover 82 is then passed through the inner hole of the blood sampling holder 78 to arrange the engagement portion 122 between the flange portion 94 and the plug portion 98 of the hub 76. The blood sampling holder 78 is thereby supported with respect to the hub 76 in a state rotatable about the axis line of the hub 76. At this stage, the assembly of the blood sampling device 10 is completed.

All the components can be assembled from the same direction according to the assembly of the blood sampling device 10 described above, whereby the assembly efficiency can be enhanced.

In the blood bag system 12 configured as above, the blood sampling needle 20 is inserted with respect to the donor with the sealing member 26 in the initial state (closed state) and the clamp 38 in the opened state. The initial flow blood that flowed out from the donor is then guided to the initial flow blood bag 33 through the blood sampling needle 20, the first tube 22, the branched connector 24, and the branched tube 32.

When the initial flow blood in the initial flow blood bag 33 reaches a predetermined amount, the clamp 38 is closed to stop the sampling of the initial flow blood to the initial flow blood bag 33. Thereafter, the initial flow blood in the initial flow blood bag 33 is transferred to the blood sampling tube 200 using the blood sampling device 10.

Specifically, the extraction tube 40 connected to the lower end of the initial flow blood bag 33 arranged in a suspended manner is curved so that an opening 142 of the blood sampling holder 78 is directed upward (see FIG. 5). The blood sampling holder 78 is rotated with respect to the hub 76 so that the open/close lid 116 of the blood sampling holder 78 does not becomes a hindrance in the task.

In this case, the cap 84 does not rotate with the blood sampling holder 78 since the cap 84 is fitted to the needle supporting unit 90 of the hub 76 independent from the blood sampling holder 78.

In other words, the cap 84 is fixed to the hub 76 under a state separated from the blood sampling holder 78, whereby even if the blood sampling holder 78 is rotated with respect to the hub 76, the cap 84 does not rotate with respect to the hub 76 accompanying the rotation of the blood sampling holder 78 and the needle cover 82 pushed by the cap 84 does not deform. Therefore, when the blood sampling holder 78 is rotated with respect to the hub 76, the externally fitted portion 140 can be prevented from detaching from the small diameter portion 104 and the large diameter portion 106.

The blood sampling tube 200 is then inserted into the blood sampling holder 78. The rubber plug 202 of the blood sampling tube 200 is then brought into contact with the distal end of the needle cover 82 to push and contract the needle cover 82 toward the hub 76. When the needle cover 82 is contracted in the longitudinal direction of the hollow needle 80, the tip of the hollow needle 80 is passed through the needle cover 82 and exposed to the outside.

Figure 6:
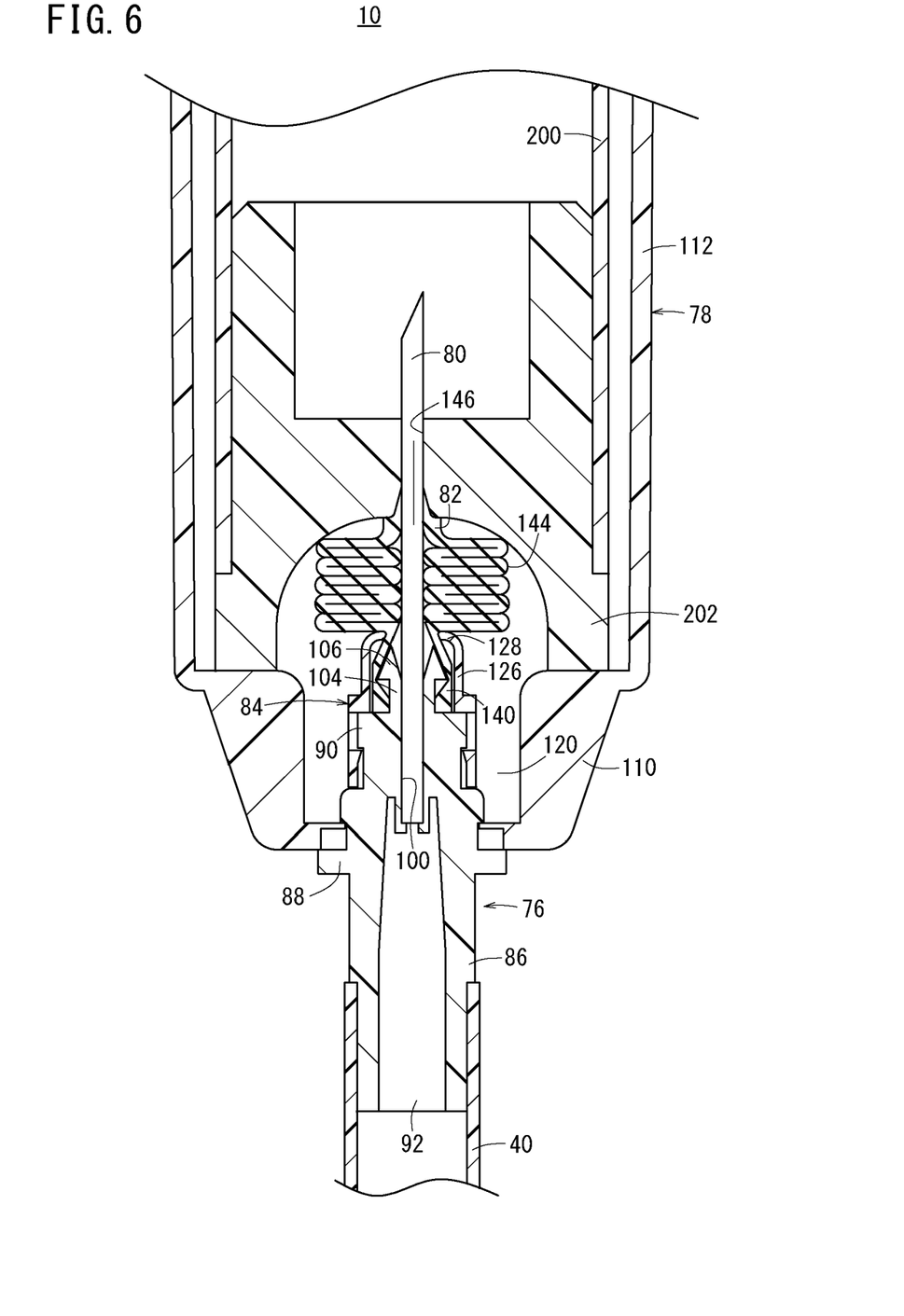
FIG. 6 is a cross-sectional explanatory view showing a state in which a hollow needle of the blood sampling device is penetrated through a rubber plug of the blood sampling tube.

As shown in FIG. 6, when the blood sampling tube 200 is further inserted toward the hub 76 side, the hollow needle 80 is penetrated through the rubber plug 202 and the needle cover 82 is elastically deformed to an accordion form toward the radially outer side of the hollow needle 80. In this case, an accordion-like elastic deforming portion 144 of the needle cover 82 makes contact with the deformation regulating portion 128, so that the accordion-like elastic deformation of the needle cover 82 does not reach the externally fitted portion 140. The distal end portion of the needle cover 82 sometimes bite into the through-hole 146 formed in the rubber plug 202.

When the tip portion of the hollow needle 80 is exposed in the blood sampling tube 200, the initial flow blood in the initial flow blood bag 33 is transferred to the blood sampling tube 200 in the depressurized state through the extraction tube 40, the initial flow blood passage 92, and the hollow needle 80.

After the transfer of the initial flow blood to the blood sampling tube 200 is completed, the blood sampling tube 200 is pulled out from the hollow needle 80. Here, the needle cover 82 is returned to the original state to cover the tip side of the hollow needle 80. Thus, the initial flow blood is suppressed from leaking out from the blood sampling device 10.

If the distal end portion of the needle cover 82 is biting into the through-hole 146 of the rubber plug 202, the needle cover 82 will be pulled by the rubber plug 202 when the rubber plug 202 is pulled out from the hollow needle 80, but the accordion-like elastic deformation does not reach the externally fitted portion 140 due to the deformation regulating portion 128, that is, the fit-in force of the externally fitted portion 140 and the small diameter portion 104 and the large diameter portion 106 is held so that the needle cover 82 is suppressed from falling out from the needle supporting unit 90.

Furthermore, since the elastic deformation of the externally fitted portion 140 is prevented by the surrounding portion 126, the needle cover 82 is less likely to fall out from the needle supporting unit 90. Moreover, since the needle cover 82 is pushed inward by the deformation regulating portion 128, the externally fitted portion 140 of the needle cover 82 is further suppressed from falling out from the needle supporting unit 90.

After the initial flow blood sampling is terminated, the breaking operation is carried out with respect to the sealing member 26 to open the flow path of the second tube 28, so that a predetermined amount of blood (whole blood) is sampled in the parent bag 30. Thereafter, the white blood cells and the blood platelets of the whole blood of the parent bag 30 are removed with the filter 48, and the remaining blood component is transferred to the first child bag 54. Using the centrifugal transfer device (not shown), the blood component of the first child bag 54 is then separated into two components, the blood plasma and the concentrated red blood cell, and the blood plasma and the concentrated red blood cell are separately accommodated and preserved in different bags (first child bag 54 and second child bag 56).

According to the present embodiment, the cap 84 is fitted to the needle supporting unit 90 independent from the blood sampling holder 78, and thus the cap 84 does not rotate along when rotating the blood sampling holder 78 with respect to the hub 76. Thus, an unnecessary stress does not act on the needle cover 82 when rotating the blood sampling holder 78 with respect to the hub 76, whereby the externally fitted portion 140 of the needle cover 82 can be prevented from detaching from the small diameter portion 104 and the large diameter portion 106.

In the present embodiment, the cap 84 that prevents the needle cover 82 from falling out from the needle supporting unit 90 is arranged, so that even if the hollow needle 80 is penetrated through the rubber plug 202 of the blood sampling tube 200 and the needle cover 82 is elastically deformed to the accordion form, the needle cover 82 can be suppressed from falling out from the needle supporting unit 90 when pulling out the rubber plug 202 from the hollow needle 80.

In other words, since the deformation regulating portion 128 that makes contact with the needle cover 82 is positioned on the tip side of the hollow needle 80 than the large diameter portion 106 of the needle supporting unit 90, the accordion-like elastic deformation of the needle cover 82 can be suppressed from reaching the externally fitted portion 140. Thus, the externally fitted portion 140 can be suppressed from bulging, whereby the fit-in force of the externally fitted portion 140 and the needle supporting unit 90 is held. Therefore, the needle cover 82 can be reliably suppressed from falling out from the needle supporting unit 90.

In addition, since the deformation regulating portion 128 pushes the needle cover 82 inward, and hence the frictional force of the needle cover 82 and the needle supporting unit 90 can be increased. The needle cover 82 thus can be further reliably suppressed from falling out from the needle supporting unit 90.

Furthermore, in the present embodiment, the deformation regulating portion 128 is formed to an annular shape, so that the accordion-like elastic deformation of the needle cover 82 can be suitably suppressed from reaching the externally fitted portion 140, and the needle cover 82 can be further reliably suppressed from falling out from the needle supporting unit 90.

According to the present embodiment, the cap 84 includes the surrounding portion 126 that surrounds the externally fitted portion 140 of the needle cover 82, and thus the externally fitted portion 140 can be suitably suppressed from bulging. The fit-in force of the externally fitted portion 140 and the needle cover 82 is thereby reliably suppressed from lowering, and the needle cover 82 is more unlikely to fall out from the needle supporting unit 90.

The lock portion 124 of the cap 84 is securely fixed with respect to the needle supporting unit 90, and the accordion-like elastic deformation of the needle cover 82 can be suitably suppressed from reaching the externally fitted portion 140 by the diameter reduced deformation regulating portion 128, whereby the needle cover 82 can be more effectively suppressed from falling out from the needle supporting unit 90.

In the description made above, the suitable embodiments have been described for the present invention, but the present invention is not limited to the embodiments described above, and it should be recognized that various modifications can be made within a scope not deviating from the gist of the invention.

For example, the deformation regulating portion 128 may be brought proximate to the needle cover 82 in a non-contacting manner with the blood sampling device 10 in the assembled state. In other words, the deformation regulating portion 128 can be brought into contact with the elastic deforming portion 144 so that when the needle cover 82 is elastically deformed to the accordion form, the elastic deformation does not reach the externally fitted portion 140.

The fit-in mode of the hub 76 and the cap 84 is not limited to the structure described above. For example, the hub 76 may be formed with one annular protrusion in place of the fit-in protrusions 108a to 108d. In this case, for example, the cap 84 may be formed with an annular groove that can be fitted to the annular protrusion in place of the fit-in holes 130a to 130d described above. According to such fit-in mode, the circumferential position of hub 76 and the circumferential position of the cap 84 do not need to be aligned, and the cap 84 can be assembled with respect to the hub 76 at an arbitrary position in the circumferential direction, whereby the number of assembly steps of the blood sampling device 10 can be reduced.

The fit-in holes 130a to 130d may not be formed in the cap 84. In other words, the cap 84 may include a fit-in portion that can be fitted to the fit-in protrusions 108a to 108d of the hub 76.

Furthermore, even if the fit-in holes 130a to 130d are formed in the cap 84, the number of fit-in holes 130a to 130d and the number of fit-in protrusions 108a to 108d do not need to be the same. For example, one fit-in protrusion may be arranged on the hub 76 and two fit-in holes may be formed in the cap 84. If the number of fit-in holes is larger than the number of fit-in protrusions, the position of the fit-in protrusion and the position of the fit-in hole can be easily aligned in the circumferential direction compared to when the same number of fit-in protrusions and fit-in holes are arranged, and hence the number of assembly steps of the blood sampling device 10 can be reduced.

A fit-in groove (fit-in hole) may be formed with respect to the hub 76 and a fit-in protrusion that can be fitted to the fit-in groove may be formed with respect to the cap 84.

The invention claimed is:

1. A blood sampling device comprising:
   a blood sampling holder to which a blood sampling tube is insertable;
   a hollow needle that penetrates through a plug member of the blood sampling tube;
   a hub that includes a supporting unit for supporting a base end side of the hollow needle, said supporting unit comprising a small diameter cylindrical portion and a large diameter portion, the large diameter portion is a frustro-conical shape having a larger diameter base adjacent the small diameter cylindrical portion and narrows to a smaller diameter tip end at a distal end of said support unit, and to which the blood sampling holder is rotatably attached;
   a needle cover made of rubber that is externally fitted to the supporting unit while covering a tip side of the hollow needle; and
   a cap mounted on the supporting unit of the hub such that the allows rotation of the blood sampling holder with respect to the hub, the cap having a first annular portion for capturing the needle cover between the supporting unit and the cap adjacent a distal end of the needle, wherein the cap includes a second annular portion positioned proximally from the first annular portion where the second annular portion pushes inwardly against the needle cover and said tip end of supporting unit and said second annular portion touches the needle cover both when the needle cover is covering the tip side of the needle and when the tip side is exposed through the needle cover to prevent the cover from expanding between the second annular portion and the first annular portion.

2. The blood sampling device according to claim 1, wherein the cap includes a tubular portion that surrounds an externally fitted portion of the needle cover adjacent the supporting unit of the hub.

3. The blood sampling device according to claim 1, wherein the cap includes
   a lock portion adapted to connect the cap to the hub toward a base end of the supporting unit.

4. The blood bag sampling device according to claim 3 wherein the lock portion of the cap comprises a tubular wall, and further comprises a plurality of holes in said tubular wall of the cap and protrusions on said hub, said protrusions being adapted to engage said holes.

5. The blood bag sampling device according to claim 1, wherein the second annular portion curves inwardly to push the needle cover against the tip end of the supporting unit and forms a gap between the cap and needle cover.

* * * * *